United States Patent
Bruto Da Costa

(10) Patent No.: US 8,403,843 B2
(45) Date of Patent: Mar. 26, 2013

(54) ATTACHABLE PORTABLE ILLUMINATION APPARATUS FOR SURGICAL INSTRUMENTS

(76) Inventor: Fernando Antonio Cepeda Bruto Da Costa, Lisboa (PT)

(*) Notice: Subject to any disclaimer, the term of this patent is extended or adjusted under 35 U.S.C. 154(b) by 237 days.

(21) Appl. No.: 12/526,393

(22) PCT Filed: Feb. 4, 2008

(86) PCT No.: PCT/PT2008/000008
§ 371 (c)(1),
(2), (4) Date: Aug. 7, 2009

(87) PCT Pub. No.: WO2008/097119
PCT Pub. Date: Aug. 14, 2008

(65) Prior Publication Data
US 2011/0004068 A1     Jan. 6, 2011

(30) Foreign Application Priority Data
Feb. 7, 2007   (PT) .......................... 103654

(51) Int. Cl.
*A61B 1/06*     (2006.01)
(52) U.S. Cl. ........................ 600/249; 362/572
(58) Field of Classification Search .................. 600/249; 362/285, 572–575, 577–579, 109–120, 572–279
See application file for complete search history.

(56) References Cited

U.S. PATENT DOCUMENTS

| | | | | |
|---|---|---|---|---|
| 2,625,645 A * | 1/1953 | Crane | ............................ | 362/116 |
| 6,009,779 A * | 1/2000 | Mastroni | ......................... | 81/438 |
| 6,220,720 B1 * | 4/2001 | Stephens | ........................ | 362/205 |
| 6,428,180 B1 * | 8/2002 | Karram et al. | ................. | 362/119 |
| 2001/0046652 A1 * | 11/2001 | Ostler et al. | ..................... | 433/29 |
| 2005/0063177 A1 | 3/2005 | Correa | | |
| 2005/0090851 A1 | 4/2005 | Devlin | | |
| 2005/0171407 A1 * | 8/2005 | Rosenkranz et al. | .......... | 600/249 |
| 2006/0189849 A1 * | 8/2006 | Sharratt et al. | ................ | 600/249 |
| 2006/0250798 A1 * | 11/2006 | Herold | ............................ | 362/280 |
| 2007/0019400 A1 * | 1/2007 | Clausen et al. | ............... | 362/109 |

FOREIGN PATENT DOCUMENTS

| | | |
|---|---|---|
| DE | 20 2004 002 963 U1 | 4/2004 |
| GB | 2 376 520 A | 12/2002 |
| WO | 01/06176 A1 | 1/2001 |
| WO | 02/47541 A2 | 6/2002 |
| WO | 2004/080291 A2 | 9/2004 |
| WO | 2005/094712 A1 | 10/2005 |

* cited by examiner

*Primary Examiner* — Ellen C Hammond
*Assistant Examiner* — Jacqueline Johanas
(74) *Attorney, Agent, or Firm* — Sughrue Mion, PLLC

(57) ABSTRACT

An illumination apparatus is attachable to surgical instruments, and provides illumination of the operating field, particularly those requiring good illumination of normally poorly illuminated organ cavities, during surgical procedures. The illumination apparatus includes a light source (1) connected to a power supply (2). The light source (1) and part or all of the power supply source are housed in a casing (3) that has at least one attaching means (5) on its outer surface which is suitable for removably attaching the illumination apparatus to a surgical instrument, and desirably, to several different surgical instruments at various times during a particular surgical procedure. Due to its weight, design and size, the illumination apparatus allows for easy shifting of the illumination apparatus along the surgical instrument without interfering with the normal use of the surgical instruments.

15 Claims, 6 Drawing Sheets

ATTACHABLE PORTABLE ILLUMINATION APPARATUS FOR SURGICAL INSTRUMENTS

TECHNICAL FIELD

The present invention relates to an illumination apparatus, in particular a portable illumination apparatus capable of being easily attached, removed and re-attached to different surgical instruments and providing a localized light in the operating field.

BACKGROUND ART

It is a well known fact that surgical procedures require the surgeon to have an enormous degree of care and precision when performing the operation. In order to operate with precision it is a fundamental condition that the surgeon has access to good lighting, especially when operating on cavities and recesses inside the body which are normally difficult to see.

Surgeons and medical professionals have been seeking improved illumination solutions for a long time and various solutions have been proposed in the past, as will be discussed below.

The modern traditional and basic lighting system is based on the use of strong overhead lights or projectors that are located relatively far away from the operating field. At present, these are normally large heavy lights fixed to the ceiling of the operating room or fixed to a stand near the operating table. This system, which is still an obligatory piece of equipment in any modern operating room (and should remain so in the future), has several disadvantages associated with it. Firstly, this type of light source does not always enable a focused light on the targeted area, such as recesses and cavities in the human body which are by nature difficult to see. This problem is compounded by the fact that sometimes, the surgeon's hands, shoulders and head get in the way of the light, which creates shadows in the operating field. These large powerful lights also generate a lot of heat, which can often place the surgeons and other medical staff at some discomfort.

Although said overhead lights should, and most probably will, remain essential equipment in any modern operating room, they should be complemented by other more localized lighting methods.

Due to the shortcomings of the overhead lights and with the objective of bringing the light source closer to the operating field, other lighting systems have been developed that consist in strapping a light to the surgeon's head cap. Presently, the light source of this system is done with fiber optics, but in the past other lighting solutions, such as incandescent light bulbs, have been proposed.

This lighting method, although also extremely useful and generally beneficial for surgeons, does has the disadvantage of forcing the surgeon to move his head and neck in order to make the light shine on the area where he wishes to operate. In addition, this sort of apparatus is relatively heavy to carry on one's head for long periods of time, which can negatively affect the surgeon's performance, particularly during a long operation. The headlights also do not resolve many of the same the problems related to the overhead room fixed lights, such as the creation of shadows when hands and other objects are placed in the path of the light.

U.S. Pat. No. 6,585,727 describes a lighting solution that includes specifically designed medical instruments that can temporarily receive a fiber optic cable which provides illumination to the surgical pocket. This system, although providing a better illumination of the targeted area, has many disadvantages, namely it is excessively complex and costly since it requires the manufacture of special dedicated surgical instruments with guides through which the fiber optic cable can pass. In addition to this being fairly difficult to do during an operation, it is also quite time-consuming, since the threading of a cable through small guides on a surgical instrument is something that takes time and dexterity. The disclosed solution would most definitely not be adequate for emergency situations. Lastly, this system also has the disadvantage that one cannot alter easily the position and angle of the light source.

WO 02/07632 provides another different approach to solve the problem of lighting the surgical pocket. This invention consists of a lighting apparatus that is attached to the actual inside of the patient's body through stitches and other traumatic techniques, which techniques are complicated and may even violate the basic therapeutic principle of "primum non nocere." There are innumerous shortcomings and disadvantages associated to this system, namely the complexity, cost and volume of the apparatus. In addition, the fact that this apparatus operates on batteries means that there is the additional necessity of verifying that the batteries are charged before surgery begins. This means additional workload and worries for the health care providers and equipment maintenance teams.

In US-2005/063177 to CORREA, Carlos et al, an illumination assembly usable with a plurality of devices which includes a light source having one or more light generating elements, preferably LED's is disclosed. This illumination assembles provides a solution that due to its specific configuration is not suitable for open-sky surgeries, not providing easy adjustment of the angle of the light, sliding and easy repositioning. During the surgery, transfer of the assembly from one instrument to another cannot be easily performed without the help WO-2005/094712 discloses a surgical light comprising a plastic moulded element having a compartment for a magnet and another compartment for a LED. This light is conceived to be adhered to a surgical retractor by magnetic attraction and is not adaptable to surgical instruments. It aims the solving of problems of disposability, price and materials and not of lightning. The size and weight are a considerable problem and the magnets must be strong enough to support the weight of the light without slipping.

A method and systems for medical and surgical lighting systems is disclosed in WO-2004/080291, including methods and systems wherein semiconductor illumination light sources are integrated into surgical tools for providing controlled lighting to a work area, such as a body cavity. However this system has several drawbacks namely that they are complex, fixedly attached or embedded into the surgical instrument.

OBJECT OF THE INVENTION

It is an object of the present invention to provide a small mobile illumination apparatus that provides an extremely localized light close to the precise area where a surgeon is operating and in which said apparatus can be easily and rapidly attached to various surgical instruments, one at a time, during the operation.

It is still yet another object of the present invention to provide an illumination apparatus that can be used to recover or attract metallic objects within the surgical pocket.

SUMMARY OF THE INVENTION

The illumination apparatus according to the present invention is comprised, in its most basic embodiment, of the following components: a light source, an energy supply source, some connection means between the latter two components, a housing casing and at least one magnetic attaching means capable of attaching the illumination apparatus to several different surgical instruments, one at a time.

The light source can be any suitable light source provided that it supplies the necessary luminosity and is sufficiently small that it can be held in the casing according to the present invention. In a preferred embodiment of the invention, the light source is one that emits very little heat when in use yet emits a light intensity equal or superior to 10 000 mili-candela (mCD). In a particularly preferred embodiment, the light source is a Light Emitting Diode (LED).

The said light source is housed in one end of a specifically designed casing. Said casing can assume various different forms and shapes provided that it has at least one opening through which the light emitted from the light source can pass out of the casing. In a preferred embodiment of the invention, the housing casing comprises a two piece assembly hollow main body with an essentially conical shape with parallel flat ends. The said casing is divided into two parts, as is well known in the art of casing moulds.

Attached to said main body is an attachment flap that projects itself along an imaginary line that is tangential in relation to a point on the circumference of the main body. The shape of said main body and attachment flap seen together from a frontal view resembles the letter b. Said attachment flap may be a separate component which is removably or permanently fixed to the said main body or, in a particularly preferred embodiment, may be a integral part molded together with one of halves of the main body.

All edges of said casing are rounded so as to not snag or tear any tissue inside the human body during a surgical operation.

The essentially conical main body must, as mentioned, be hollow in order to house the light source and all or part of the energy supply source and the respective connection means. Given its hollow nature, the casing main body has inner walls and an outer shell. Inside the hollow main body and, in close proximity to the said open end for the passage of light, the inner wall of the said main body has several small seats specifically configured to secure and clamp the light source in place and prevent it from shifting inside the casing. The light emitting end of the light source will naturally be directed towards the exterior just beyond the open end of the casing so that the light may shine out of the casing. Each side of the two piece assembly of the main body will have some connection means that will permit them to be fitted together. Such as is customary in these sorts of structures, this connection means may be provided through small projections on the inner wall of one half of the main body that are inserted into corresponding holes on the other half of the main body.

In a particular embodiment of the present invention in which the light source is connected to an external energy supply source, the casing will also have a second, smaller opening on the opposite end in relation to the main open end, said smaller opening being necessary for the passage of the connection means that connect the light source to the external power supply source.

The casing according to the present invention must be preferably made from a moldable material, yet be relatively rigid and durable. The material must also, as would be obvious to those skilled in the art, be deemed medically adequate, light weight and easy to clean and sterilize, if necessary. In a particularly preferred embodiment of the invention, the housing casing is made of some type of plastic, such as polyurethane. In another less preferred embodiment, the housing casing is made of medically suitable metal or metal alloy.

The illumination apparatus according to the present invention has at least one attaching means that permits the said casing of the apparatus to be easily attached and removed from surgical instruments. In a preferred embodiment of the invention, the casing has three or more attaching means which are fixed to the outer shell of the casing or to the sides of the flap that projects itself outwards from the main body of said casing. In a particularly preferred embodiment of the invention, these attaching means are small disc-shaped magnets fixed to the attachment flap of the casing. The method by which the attaching means are fixed to the outer shell of the casing main body or the flap can assume a variety of forms. For example, the attaching means may be embedded on the outer surface or snapped into some purpose-built recesses on the same surface. Alternatively, the attaching means may be glued or retained in their position through the use of some other fixing means such as clips, pins etc., all of which are well known in the state of the art.

The attaching means according to the present invention are ideally magnets since their magnetic properties make them easy to attach and remove from surgical instruments, the vast majority of which are metallic. These same magnetic properties are also convenient for attracting and removing small metallic objects such as needles that often fall during operations. As is also well known by those skilled in the art, the existence of several magnets and additionally the passage of an electric current past them transfer magnetic properties to other metallic objects that are in contact with them. Therefore, when the illumination apparatus of the present invention is magnetically attached to a metallic surgical instrument, and current is passed through the illumination apparatus, this will result in the actual surgical instrument acquiring some magnetic properties and thus be suitable for attracting other small metallic objects, such as needles.

In a preferred embodiment of the invention, the open end of the casing close to which the light source is housed has a transparent cap that is removably attached to the casing. Said transparent cap may be made of glass or, more preferably, from a clear material that is less susceptible to shattering such as transparent acrylic. The said cap can be attached to the open end of the casing in a variety of manners. In one preferred embodiment, the border of the open end of the casing will have a groove or recess that runs around the inner circumference of the casing circular open end, said groove being adapted for accommodating the edges of the transparent cap and maintaining it in a fixed position. In an alternative embodiment, the transparent cap is a threaded cup-shaped cap that can be snapped into position or alternatively screwed into a corresponding internal thread in the open end of the casing. The manner in which the transparent cap is fixed to the casing can assume other configurations all of which are well known methods and do require explaining. The obligatory characteristics that the transparent cap must have are durability and rigidity so that the cap does not break and shatter when in use. The cap must be totally transparent in order not to impede the passage of light. In a particularly preferred embodiment, the transparent cap has surfaces that do not alter the direction of the light rays emitted from the light source. However, other alternative embodiments that foresee concave or convex-shaped caps are also deemed to be included in this invention.

The fundamental characteristic of the transparent cap is that it should sealably close the open end of the illumination apparatus casing so as not to allow the entry of any substances into said casing. This, should it occur, may not only affect the projection of light but also the very operation of the apparatus.

As was mentioned above, in an embodiment of the invention in which there is an external power supply, the casing end opposite to the open end that houses the light source may also have a small opening to allow the connection means to pass from the inside of said casing to the exterior. Said connection means, which consists of electrical wiring, connects the light source to the energy supply source and thus conveys energy from one element to the other. For safety purposes, the electrical power conveyed through the wiring should be low tension/low voltage so as to not put the health of the patient or the surgeon that handles the apparatus at risk in any way. Low tension electric energy has the advantage of supplying the lighting apparatus with an endless and continuous power supply and, therefore, a light that does not fade or stop. The connection means between the light source and energy supply source may also have a switch which can permit or prevent the flow of electricity through the connection means.

In an alternative embodiment of the invention, the apparatus casing does not have a rear small opening and is designed to carry one or more batteries that provide the power necessary for the light source. This embodiment has advantages over the previous in that it provides greater mobility and the possibility to use the apparatus in emergency operations in which no access to a power socket is possible. One such situation is an emergency operation in a combat zone or disaster relief.

Whether the illumination apparatus of the present invention is battery operated or powered by electricity from a power grid, either option is perfectly viable with regards to medical instruments and, indeed, both these methods of energy supply are extremely frequent to many existing medical apparatuses.

The advantages of the present invention over the previous state of the art are numerous. Firstly, the illumination apparatus provides a very localized and focused light source very close to the area targeted by the surgeon. Since the light source is placed in close proximity to the tip of the surgical instrument that the surgeon is handling, there is virtually no possibility of other objects getting in the way and preventing light rays to pass and thus causing shadows. The localized light provided by the apparatus of the present invention does not mean that other light sources are not necessary in the operating room to give an overall good illumination. However, the present apparatus means that it is no longer necessary to constantly move overhead lights or the surgeon to move his head or neck in order to redirect his head light, as is frequent in present operations. The fact that the illumination apparatus is attached to the surgical instrument that the surgeon is handling means that the light source of the apparatus will provide very localized illumination on cavities and recesses inside the human body that are normally dark and hard to see with the light provided by the traditional lighting techniques. The localized illumination provided by the apparatus of the present invention also has teaching and learning merits since with the additional light, the surgeon can visualize more clearly the shapes of the body parts he is operating on and thus perform the procedures with greater confidence and reliability.

The second major advantage of the present invention over the prior art is the flexibility, adaptability and user-friendliness of the apparatus. The apparatus according to the present invention is truly movable and adaptable to standard existing surgical instruments. Whereas before the prior art revolved around manufacturing specifically designed surgical instruments, the present invention, by using magnets as attaching means that are fixed to the casing of the apparatus, allow the surgeon to easily magnetically attach the illumination apparatus to a certain surgical instrument he is about to use. The surgeon can also shift and adjust the angle of the light by re-positioning the illumination apparatus on the instrument. For example, if the surgeon requires a more intense light on a certain area, he can easily slide the apparatus down the surface of the surgical instrument so that the light source is closer to the targeted area. This leads to more control and an improvement to existing surgical techniques. When the surgeon switches instrument he can easily remove the illumination apparatus and magnetically re-attach it to another instrument and so forth. The ability of the surgeon to do these exchanges himself instead of relying on others also results in the simplification of procedures in the operating room.

The present invention is also extremely cost efficient. The speed with which the surgeon can exchange the illumination apparatus from one instrument to another results in less assistance being required around him, which in turn means less people in the operating room. Through this new method, surgical procedures will also become slightly faster since the surgeon can work at a greater speed and with greater control. This will also have repercussions on the cost of surgeries.

The apparatus in itself is very inexpensive since it consists of very few components, all of which are relatively easy to manufacture or are readily available on the market. The low cost of the illumination apparatus is also an advantage since aside from the economic gains this represents for the hospitals, it also opens up the possibility of the hospital administration deciding between sterilizing the apparatuses for later re-use or, alternatively, opt to simply discard them after use.

The adaptability of the illumination apparatus in the battery operated embodiment of the present invention has great advantages when used in emergency surgeries or by doctors in conflict areas where other lighting solutions is not possible or not available. In extreme situations, the present apparatus can even be used with no other light source.

Lastly, as has already been mentioned above, the other advantage of the present invention is that the illumination apparatus, when in use, creates a magnetic field that is useful for attracting and recovering small metallic objects. In practical terms, this is a great advantage in situations where it is necessary to recover quickly metallic objects such as needles or scissors that have fallen into body cavities and the surgical pocket in general.

It is important to note that the advantages of the illumination apparatus apply only to open-air surgeries and the apparatus is not conceived other types of procedures.

BRIEF DESCRIPTION OF THE DRAWINGS

Further characteristics, advantages and details of the attachable illumination apparatus according to the present invention will become more apparent hereinafter from the following disclosure with reference to the accompanying drawings, in which is shown a preferred inventive embodiment of the illumination apparatus according to the present invention.

In the drawings.

DETAILED DESCRIPTION OF A BEST MODE EMBODIMENT

Figure 1:
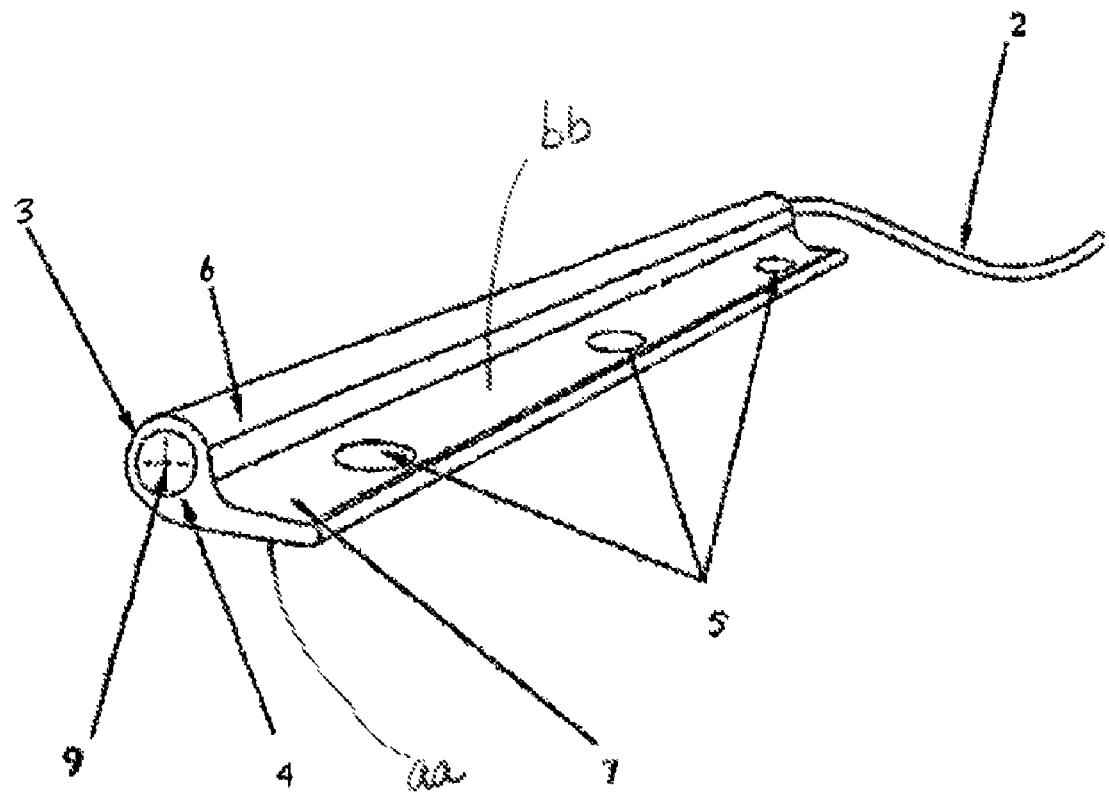
FIG. 1 shows a perspective view of the illumination apparatus of the present invention.
Figure 2:
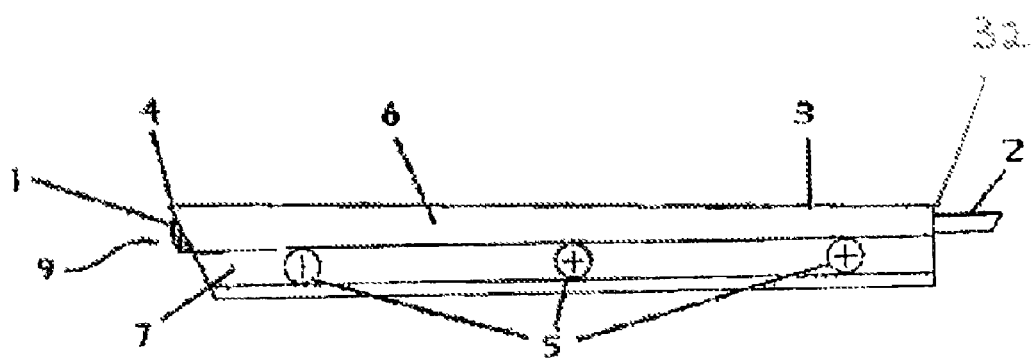
FIG. 2 shows a top plan view of the same illumination apparatus.
Figure 3:
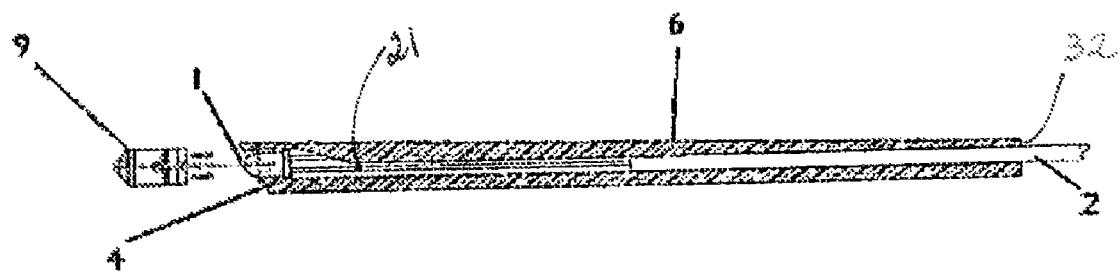
FIG. 3 shows a side cross-sectional view of the aforementioned illumination apparatus.

A concrete embodiment of the present invention consists of an illumination apparatus that is designed for use in surgical procedures. The illumination apparatus comprises a light source (1) that in this embodiment is a Light Emitting Diode (LED). This Light Emitting Diode should have an intensity or brightness of at least 10,000 milicandela (mCD). Although other light sources are possible, provided they do not put the patient's health or the operation at risk, the LED has the advantage of being very small, emitting very little heat and have excellent longevity and durability characteristics. The LED (1) is connected in the usual fashion to power supply source (2). This power supply should ideally be a low tension electrical current provided by transforming the power grid current into a lower voltage current (approximately 3 volts). The connection between the LED (1) and the power supply source (2) is provided in this embodiment by wiring (21) and contacts as is well known in the field of electrical engineering. A switch may or may not be incorporated in the wiring in order to make it possible to turn on and off the LED. The wiring should be connected to a transformer (not illustrated) that reduces that voltage of the grid network electrical current. The wiring (21) that connects the LED (1) and the power supply source (2) passes from the interior of the casing (3) to the exterior through a small opening (32) on the casing end opposite the open end designed for the passage of light. This small opening (32) is just large enough for permitting the wiring (21) to pass there through and it also includes a seal (not illustrated) that prevents liquid substances from entering the casing (3). The option for a connection to the grid network is that this solution provides an endless and continuous power supply, while other options such as a battery operated apparatus has some disadvantages as has been described above. In addition, many modern surgical tools are today electric and connected to the grid power supply which means that surgeons are familiar with the operation and logistics involved in this.

The LED (1) is housed in the specifically designed elongated casing (3) with inner walls and an outer shell. In this specific example, the casing is a modeled part made from a light metal alloy or polyurethane. The truncated-conical shaped casing (3) comprises a hollow main body (6) which is divided into two halves as is frequent practice in the art. Said main body (6) also has an essentially rectangular flap (7) that projects itself along an imaginary line that is tangential in relation to a point on the circumference of the main body. The shape of said main body and attachment flap seen together from a frontal view resembles the letter b (i.e., a cross section of the casing, taken in a direction perpendicilar to the longitudinal direction is b-shaped. Said attachment flap may be a separate component which is removably or permanently fixed to the said main body or, in a particularly preferred embodiment, may be an integral part molded together with one of halves of the main body.

All the casing outer shell surfaces are smooth and edgeless in order to make the illumination apparatus harmless when used. The absence of corners and edges means that there is no risk of the illumination apparatus being responsible for snagging or tearing and human tissue.

The end of the hollow main body (6) with the largest circumference is an open end (4) designed to house the LED (1). As is obvious to those skilled in the art, the LED must be placed and secured in the casing with the light emitting end facing outwards towards the open end (4) of the casing (3), thus allowing the light emitted to shine out of the casing in an unobstructed manner. The LED is secured to its position inside the casing by the configuration of the internal walls of the casing. Said internal wall comprise smaller walls perpendicular to the main surface of the inner wall, said smaller perpendicular walls designed to clamp the LED into place.

In this ideal embodiment, the open end (4) of the casing (3) has a cup-shaped cap (9) made of a transparent acrylic. Said cap (9) may be removably fixed to the open end (4) of said casing (3) by snap-fitting the cap (9) into an internal annular groove (not illustrated) made along the inner circumference close to the border of the open end (4), the circumference of the cap being essentially identical to that of the open end (4) and the latter being slightly flexible so as to permit the cap (9) being snapped into place through the application of some pressure. Other solutions are possible such as threading the cap onto a corresponding thread on the open end. The purpose of said cap (9) is to close off the casing open end (4) in a sealable manner and prevent the passage of any substance, such as blood. The cap (9) protects the LED (1) and the inner hollow area of the casing (3), which in turn makes the apparatus much more hygienic and easy to clean. The use of a cap (9) also makes it possible to clean off the surface of the cap (9) in the event that some substance is preventing or hindering the passage of light.

Figure 4:
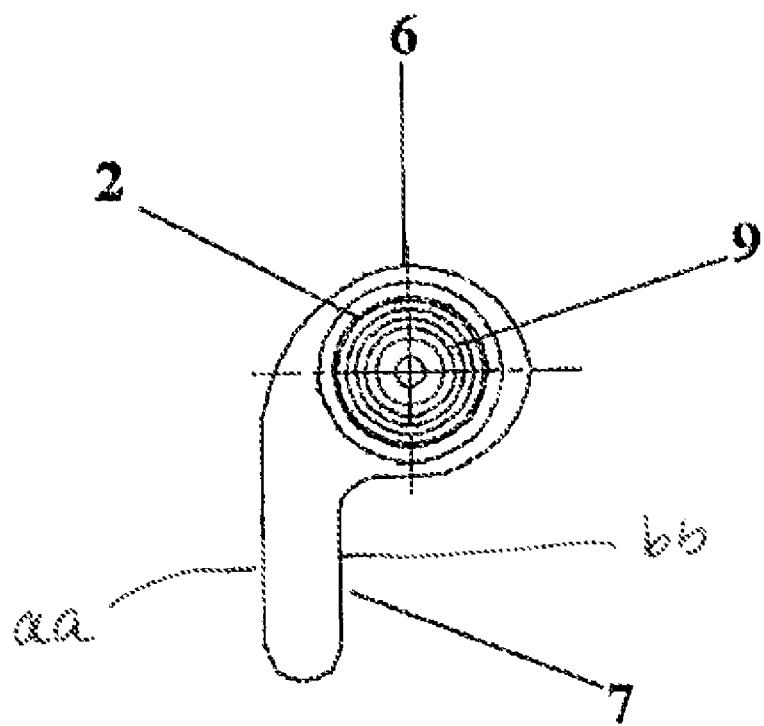
FIG. 4 shows a frontal view of the apparatus.
Figure 5:
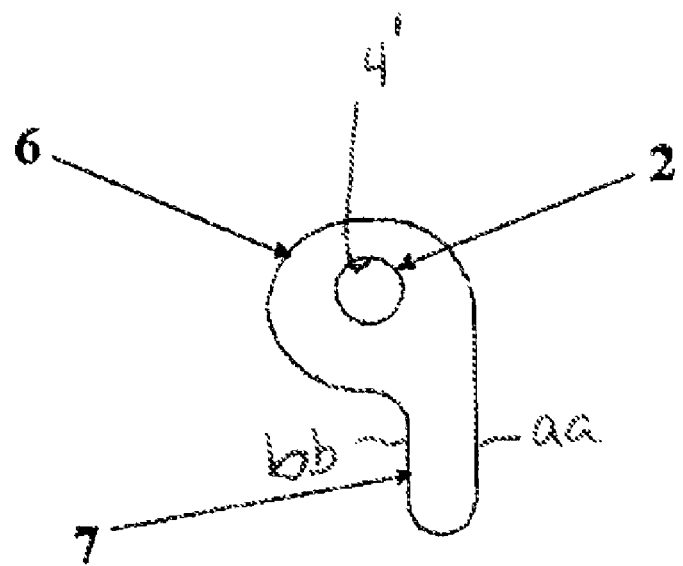
FIG. 5 shows a rear view of the apparatus.
Figure 6:
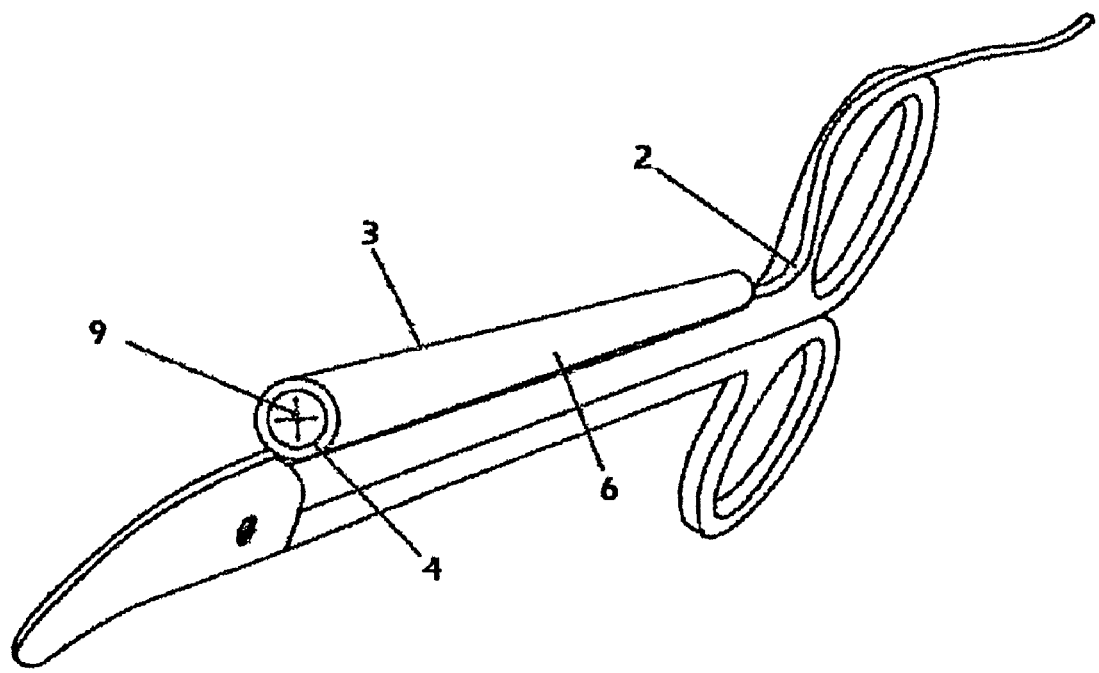
FIG. 6 shows a perspective view of the illumination apparatus attached to some surgical scissors.

In this preferred embodiment of the invention, the main body (6) of the casing (3) has a length of approximately 86 mm, a width of approximately 11 mm and thickness of approximately 7 mm at its thickest point. The main body (6) of the casing (3) also has a flap (7) that projects out from it as described above. This flap (7) is essentially rectangular albeit with rounded edges for the reasons also explained above. In a particularly desired embodiment the flap (7) has a length of 86 mm, a width of 11 mm and a thickness of 2 mm. The flap's two largest surfaces are the top and bottom planes, which for the purposes of this description, the bottom plane (aa) is that which makes a tangent to the circumference of the essentially circular main body of the casing. The top plane is the opposite surface (bb), which is parallel to the bottom plane (aa) as indicated in FIG. 4.

The top plane (bb) of the flap (7) has three circular recesses placed equidistantly from each other along the longitudinal axis of the said rectangular top plane (bb) of the flap (7). In this particularly preferred embodiment, the recesses have a diameter of approximately 5 mm and a depth of approximately 1.5 mm. In these said recesses, three disc-shaped magnets (5) are placed and therein secured. The magnets (5) may be secured in these recesses in a variety of manners that are known to those skilled in the art. These include being snapped into the recesses and maintained therein by pressure due to the design of the recesses. Alternatively, the magnets (5) may be glued into the recesses or secured by means of some additional fixing means. The single requisite of the means by which the magnets (5) are fixed is that they must retain the magnets (2) in their position on the external top plane (bb) of the flap (7). The external shell of the casing (3) may also have some recesses and magnets (not illustrated) so that in general the entire apparatus can be magnetically attached to the surgical instruments.

Due to their magnetic properties, the magnets (5) fixed to the top plane (bb) of the flap (7) and on the outer shell of the casing (3) attract metallic objects made from iron, steel, aluminum etc. They are therefore the perfect attaching means by which to removably attach the illumination apparatus to various metallic surgical instruments during a surgical procedure. The magnets (5) must be sufficiently strong to ensure that the illumination apparatus does not fall off during normal use yet also not so strong that it prevents the surgeon from being able to shift the illumination apparatus on the surgical instrument, should it be necessary. The ability to shift the illumination apparatus is essential to permit the surgeon to redirect the light emitted from the apparatus and bring said apparatus closer or further away from the targeted area. The existence of magnets (5) on the illumination apparatus results in the surgeon being able to transfer the said apparatus from one surgical instrument to another in a matter of seconds and without great physical effort. He can also attach it to any existing surgical instrument, not requiring specifically design instruments.

Due to the light weight metallic alloy or plastic material from which the casing of the illumination apparatus is made, the said apparatus weighs approximately 3.5 grams in the design conceived in the preferred embodiment. This weight will not affect in any way the normal handling of surgical instruments by the surgeons using them.

The above description of a preferred embodiment must not be interpreted as in any way limiting the scope of the protection, said protection being defined solely by the attached claims.

The invention claimed is:

1. Illumination apparatus for surgical instruments, comprising:
    a light source (1);
    a power supply source (2);
    wiring (21) for connecting said light source (1) to said power supply source (2) and supplying electric energy from said power supply source to said light source;
    a casing (3) with internal walls and an outer shell for housing and protecting said light source (1) and at least a part of said power supply source (2);
    said casing (3) comprising a hollow main body (6) and a rectangular flap, as viewed from a frontal view, attached to and projecting from the hollow main body so as to form a b-shape from the frontal view,
    wherein the hollow main body has an elongated conical shape having a front end opening (4) and a back end opening (32), the front end opening open to permit the passage of light out of the front end opening of said casing,
    wherein said rectangular flap has an outward facing planar surface (aa) and an inward facing planar surface (bb) opposite from and parallel to the outward facing planar surface (aa), said rectangular flap (7) projecting from the hollow main body (6) along an imaginary line that is tangential in relation to a point on the circumference of the main body (6); and
    at least one attaching means (5) provided with magnetic properties and fixed on the outer shell of the casing (3), allowing said casing (3) to be removably and magnetically attached to different surgical metallic instruments as needed during a surgical procedure.

2. Illumination apparatus according to claim 1, wherein the front end opening (4) of the main body (6) has a larger cross section than the back end opening (32) of the main body (6).

3. Illumination apparatus according to claim 1, wherein said front end opening (4) has a transparent cap (9) that can be removably fitted in said front end opening (4) so as to sealably close said front end opening (4) while also not preventing the passage of light emitted from the light source.

4. Illumination apparatus according to claim 1, wherein said at least one attaching means (5) is fixed to the inward facing planar surface (bb) of the flap (7) so that the inward facing planar surface is configured to contact the surgical instrument.

5. Illumination apparatus according to claim 1, wherein said casing (3) has three or more attaching means (5).

6. Illumination apparatus according to claim 1, wherein the attaching means (5) are magnets.

7. Illumination apparatus according to claim 1, wherein the light source (1) has an intensity of at least ten thousand milli-candela (mCD).

8. Illumination apparatus according to claim 7, wherein said light source (1) is a Light Emitting Diode (LED).

9. Illumination apparatus according to claim 1, wherein the power supply source (2) is one or more batteries or low current electricity provided by the electrical power grid.

10. Illumination apparatus according to claim 1, wherein the casing (3) is made from plastic, metal or metal alloy suitable for use in surgical instruments.

11. Illumination apparatus according to claim 1, wherein said apparatus weighs less than 3.5 grams.

12. Illumination apparatus according to claim 1, wherein the entire outer shell of the casing (3) is smooth and made of a magnetized metal or metal alloy that allows the casing to be removably fixed to several surgical instruments during a surgical procedure and, through magnetic forces, attract other metallic objects inside the human body being operated.

13. Illumination apparatus according to claim 1, wherein the main body (6) of the casing (3) has a length of approximately 86 mm, a width of approximately 11 mm and a thickness of approximately 7 mm at a thickest point of the casing.

14. Illumination apparatus according to claim 1, wherein the flap (7) has a length of 86 mm, a width of 11 mm and a thickness of 2 mm and three circular recesses that are provided with a diameter of approximately 5 mm and a depth of approximately 1.5 mm, placed on the inward facing planar surface (bb) of the flap (7) spaced apart along the length thereof.

15. An illumination apparatus for surgical instruments, comprising:
    a light source;
    a power supply source;
    wiring for connecting said light source to said power supply source and supplying electric energy from said power supply source to said light source;
    an elongated casing with internal walls and an outer shell for housing and protecting said light source and at least a part of said power supply source;
    said casing comprising:
        a hollow cylindrical main body and a rectangular flap attached to and projecting from the main body along an imaginary line that is tangential in relation to a point on the circumference of the main body;
        a cross-section of said casing, in a direction perpendicular to a longitudinal direction of the casing, formed in a b-shape;
        the hollow main body having a front end opening and a back end opening, the front end opening open to permit the passage of light out of the front end opening of said casing;
    at least one attaching means provided with magnetic properties and fixed on the outer shell of the casing, said casing configured to be removably and magnetically attached to different surgical metallic instruments.

* * * * *